United States Patent
Calloway et al.

(10) Patent No.: US 12,048,493 B2
(45) Date of Patent: Jul. 30, 2024

(54) CAMERA TRACKING SYSTEM IDENTIFYING PHANTOM MARKERS DURING COMPUTER ASSISTED SURGERY NAVIGATION

(71) Applicant: GLOBUS MEDICAL, INC., Audubon, PA (US)

(72) Inventors: Tom Calloway, Pelham, NH (US); Neil R. Crawford, Chandler, AZ (US)

(73) Assignee: Globus Medical, Inc., Audubon, PA (US)

( * ) Notice: Subject to any disclaimer, the term of this patent is extended or adjusted under 35 U.S.C. 154(b) by 292 days.

(21) Appl. No.: 17/657,377

(22) Filed: Mar. 31, 2022

(65) Prior Publication Data

US 2023/0310086 A1    Oct. 5, 2023

(51) Int. Cl.
*A61B 34/20*     (2016.01)
*A61B 34/00*     (2016.01)
*A61B 34/30*     (2016.01)
*A61B 90/00*     (2016.01)

(52) U.S. Cl.
CPC .............. *A61B 34/20* (2016.02); *A61B 34/25* (2016.02); *A61B 34/30* (2016.02); *A61B 2034/2055* (2016.02); *A61B 2090/3937* (2016.02); *A61B 2090/3983* (2016.02)

(58) Field of Classification Search
CPC ...... A61B 2034/2055; A61B 2090/365; A61B 2090/3916; A61B 2090/3937; A61B 2090/3983; A61B 2090/502; A61B 34/20; A61B 34/25; A61B 34/30
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |

(Continued)

OTHER PUBLICATIONS

US 8,231,638 B2, 07/2012, Swarup et al. (withdrawn)

*Primary Examiner* — Michael T Rozanski

(57) ABSTRACT

A camera tracking system for computer assisted navigation during surgery. Operations identify stray markers in a frame of tracking data from tracking cameras, and identify stray markers of a reference array. Stray markers of the reference array are designated assigned status and, otherwise, designated unknown status. The operations designate other of the assigned status stray markers and any of the unknown status stray markers along a same epipolar line of the tracking cameras as one of the assigned status stray markers as being epipolar ambiguous status. For each one of the epipolar ambiguous status stray markers, the operations estimate 3D locations where phantom markers can appear in the frame based on epipolar ambiguity of the tracking cameras when determining location of the one of the epipolar ambiguous status stray markers. The operations designate the unknown status stray markers within a threshold distance of the estimated 3D locations of phantom markers as being phantom status.

20 Claims, 6 Drawing Sheets

(56) References Cited

U.S. PATENT DOCUMENTS

| | | |
|---|---|---|
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |

(56) References Cited

U.S. PATENT DOCUMENTS

| | | |
|---|---|---|
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |

(56) References Cited

U.S. PATENT DOCUMENTS

| | | |
|---|---|---|
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |

(56) References Cited

U.S. PATENT DOCUMENTS

| | | |
|---|---|---|
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |

(56) References Cited

U.S. PATENT DOCUMENTS

| | | |
|---|---|---|
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

CAMERA TRACKING SYSTEM IDENTIFYING PHANTOM MARKERS DURING COMPUTER ASSISTED SURGERY NAVIGATION

FIELD

The present disclosure relates to medical devices and systems, and more particularly, camera tracking systems used for computer assisted navigation during surgery.

BACKGROUND

A computer assisted surgery navigation system can provide a surgeon with computerized visualization of how a surgical instrument that is posed relative to a patient correlates to a pose relative to medical images of the patient's anatomy. Camera tracking systems for computer assisted surgery navigation typically use a set of cameras to track pose of a reference array on the surgical instrument, which is being positioned by a surgeon during surgery, relative to a patient reference array (also "dynamic reference base" (DRB)) affixed to a patient. The camera tracking system uses the relative poses of the reference arrays to determine how the surgical instrument is posed relative to a patient and to correlate to the surgical instrument's pose relative to the medical images of the patient's anatomy. The surgeon can thereby use real-time visual feedback of the relative poses to navigate the surgical instrument during a surgical procedure on the patient.

During the surgical procedure, a surveillance marker is affixed to the patient to provide information on whether the patient reference array has shifted. If the surveillance marker's location changes relative to the patient reference array, the camera tracking system can display a meter indicating the amount of movement and may display a pop-up warning message to inform the user that the patient reference array may have been bumped. If the patient reference array has indeed been bumped, the registration of the patient reference array to the tracked coordinate system may be invalid and could result in erroneous navigation of the surgical instrument.

In one approach, the surveillance marker is identified to the camera tracking system by pointing with a tool having a pose tracked by the camera tracking system. If the surveillance marker is to be added by a user pointing with a tool, the software waits until a stray candidate marker is within a threshold distance (e.g., defined based on pose tracking tolerance of the tool tip) for longer than a threshold amount of time (e.g., about 2 seconds) and then registers that stray candidate marker as the surveillance marker.

In another approach, the surveillance marker is identified to the tracking system by pressing a button on a display screen. If the surveillance marker is to be added from the display screen with a single button click, there can be only one stray (unregistered) candidate marker so that software of the camera tracking system can properly select the stray candidate marker for registration as the surveillance marker.

In another approach, the surveillance marker is identified to the tracking system by a user interface where the interface shows the user all the possible surveillance marker candidates and the user selects the preferred candidate by clicking on in with a touch screen or other gesture. The system may show the surveillance marker candidates to the user in different ways. One possible way to show the candidates is to provide a 3D view with icons representing each candidate and icons representing other nearby structures such as the DRB or planned screws. Another possible way to show the surveillance marker candidates is to stream a live video to the user where they can clearly see the actual physical marker, to which the user then gestures to identify.

SUMMARY

Some embodiments of the present disclosure are directed to providing operations by the camera tracking system to improve registration of stray markers, such as a surveillance marker, when phantom markers appear in frames of tracking data from tracking cameras.

Some embodiments are directed to a camera tracking system for computer assisted navigation during surgery, which includes at least one processor that is operative to receive a stream of frames of tracking data from tracking cameras configured with a partially overlapping field-of-view. For each of a plurality of the frames in the stream, the operations identify stray markers in the frame, and identify which of the stray markers are part of a reference array. The operations designate stray markers that are part of the reference array as being assigned status, and designate stray markers that are not part of the reference array as being unknown status. For each one of the assigned status stray markers, the operations designate any other of the assigned status stray markers and any of the unknown status stray markers that are along a same epipolar line of the tracking cameras as the one of the assigned status stray markers as being epipolar ambiguous status. For each one of the epipolar ambiguous status stray markers, the operations estimate 3D locations where phantom markers can appear in the frame based on epipolar ambiguity of the tracking cameras when determining location of the one of the epipolar ambiguous status stray markers. The operations designate any of the unknown status stray markers within a threshold distance of the estimated 3D locations of the phantom markers as being phantom status, and include in a candidate registration set the unknown status stray markers that do not have phantom status.

Some embodiments are directed to a related method by a camera tracking system for computer assisted navigation during surgery. The method receives a stream of frames of tracking data from tracking cameras configured with a partially overlapping field-of-view. For each of a plurality of the frames in the stream, the method identifies stray markers in the frame, and identify which of the stray markers are part of a reference array. The method designates stray markers that are part of the reference array as being assigned status, and designates stray markers that are not part of the reference array as being unknown status. For each one of the assigned status stray markers, the method designates any other of the assigned status stray markers and any of the unknown status stray markers that are along a same epipolar line of the tracking cameras as the one of the assigned status stray markers as being epipolar ambiguous status. For each one of the epipolar ambiguous status stray markers, the method estimates 3D locations where phantom markers can appear in the frame based on epipolar ambiguity of the tracking cameras when determining location of the one of the epipolar ambiguous status stray markers. The method designates any of the unknown status stray markers within a threshold distance of the estimated 3D locations of the phantom markers as being phantom status, and includes in a candidate registration set the unknown status stray markers that do not have phantom status.

Other camera tracking system and corresponding methods and computer program products according to embodiments of the inventive subject matter will be or become apparent to one with skill in the art upon review of the following drawings and detailed description. It is intended that all such additional camera tracking system, methods. and computer program products be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

DETAILED DESCRIPTION

Figure 1:
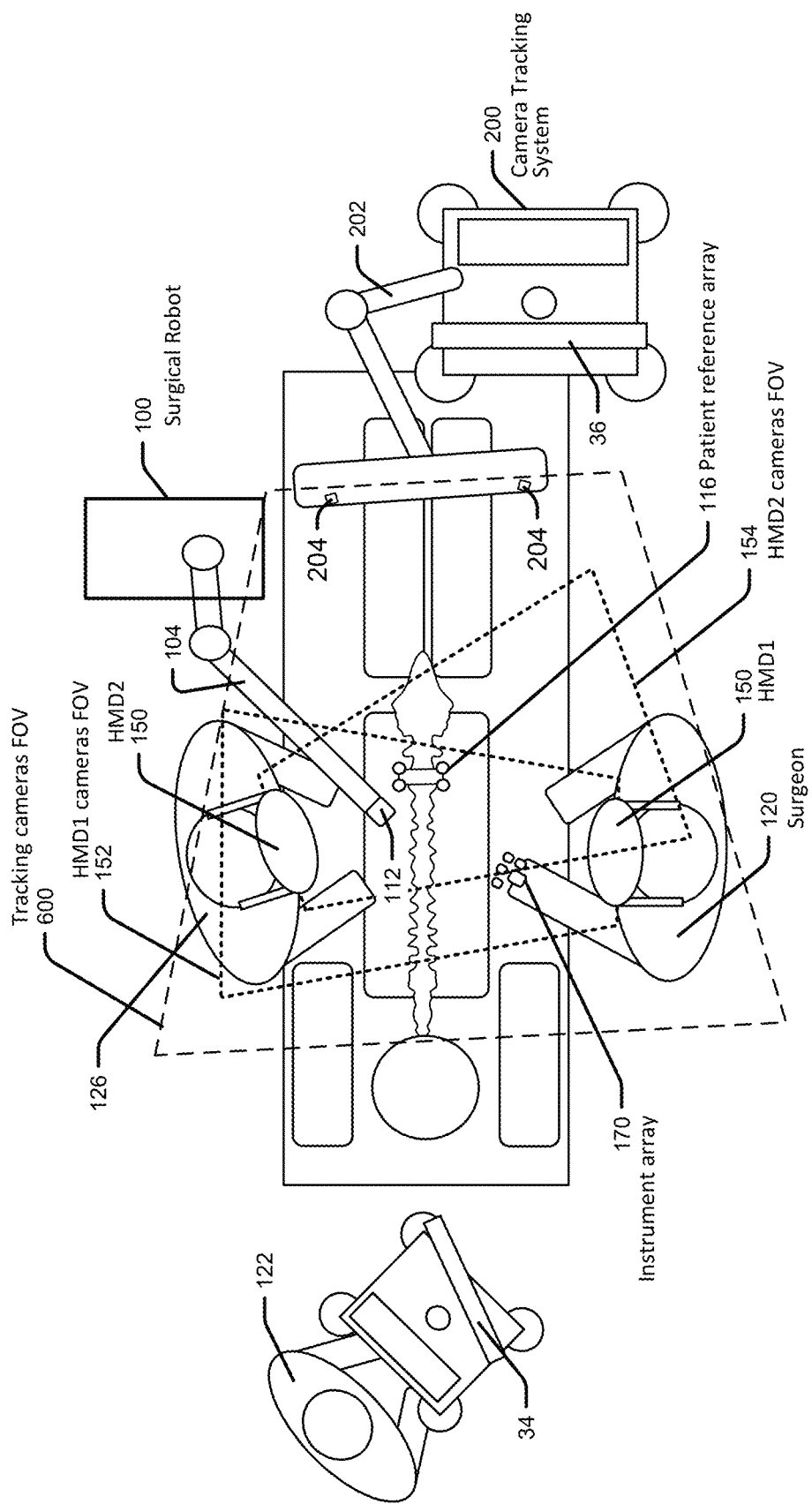
FIG. 1 is an overhead view of personnel wearing extended reality (XR) headsets during a surgical procedure in a surgical room that includes a camera tracking system for navigated surgery and which may further include a surgical robot for robotic assistance according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Various embodiments of the present disclosure are directed to providing operations by the camera tracking system to improve registration of candidate markers, such as a surveillance marker, when phantom markers appear in frames of tracking data from tracking cameras. Before describing these embodiments is detail, various components that may be used for performing embodiments in a navigated surgery system are described with reference to FIGS. 1-5.

Figure 2:
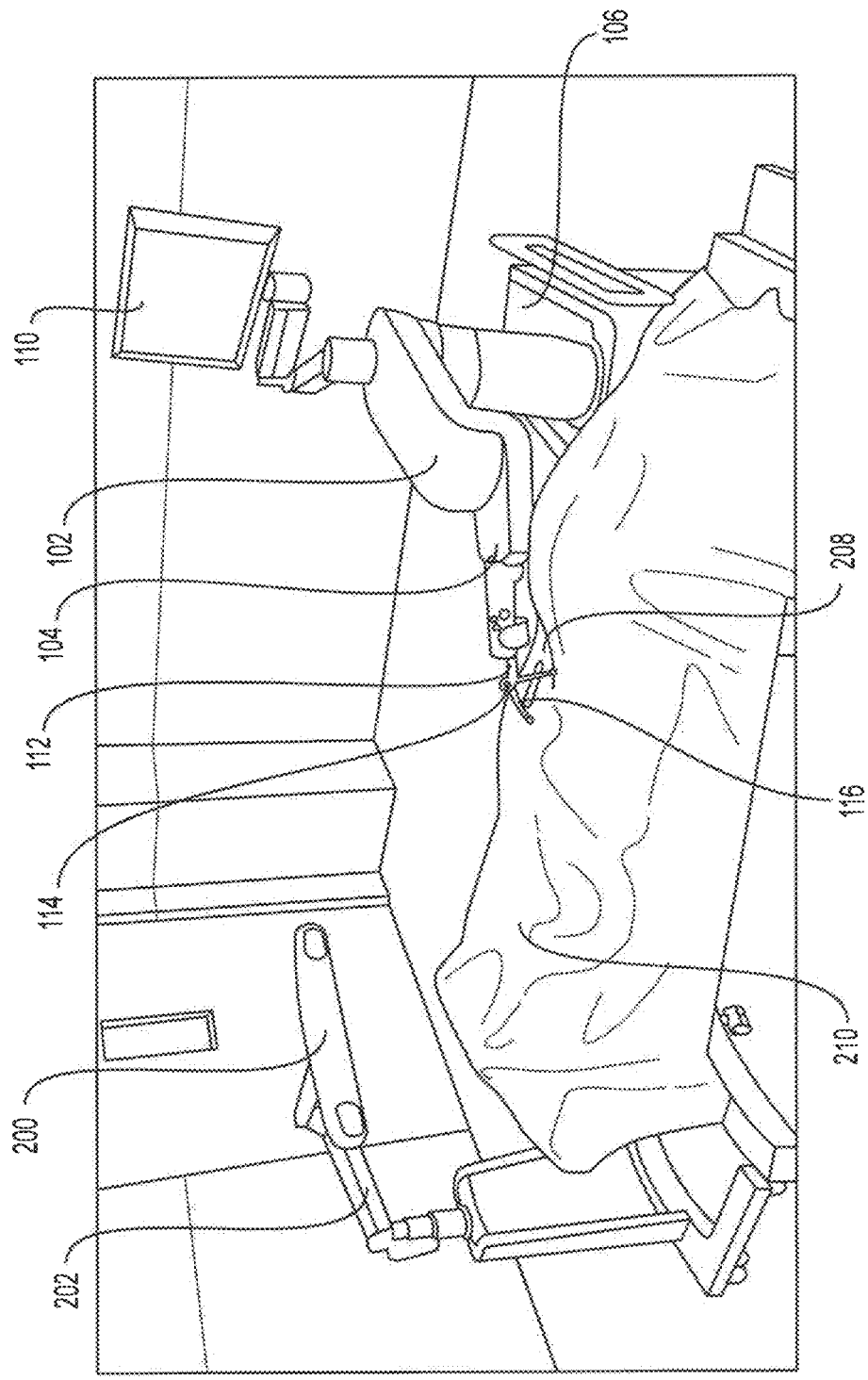
FIG. 2 illustrates the camera tracking system and the surgical robot positioned relative to a patient according to some embodiments.
Figure 3:
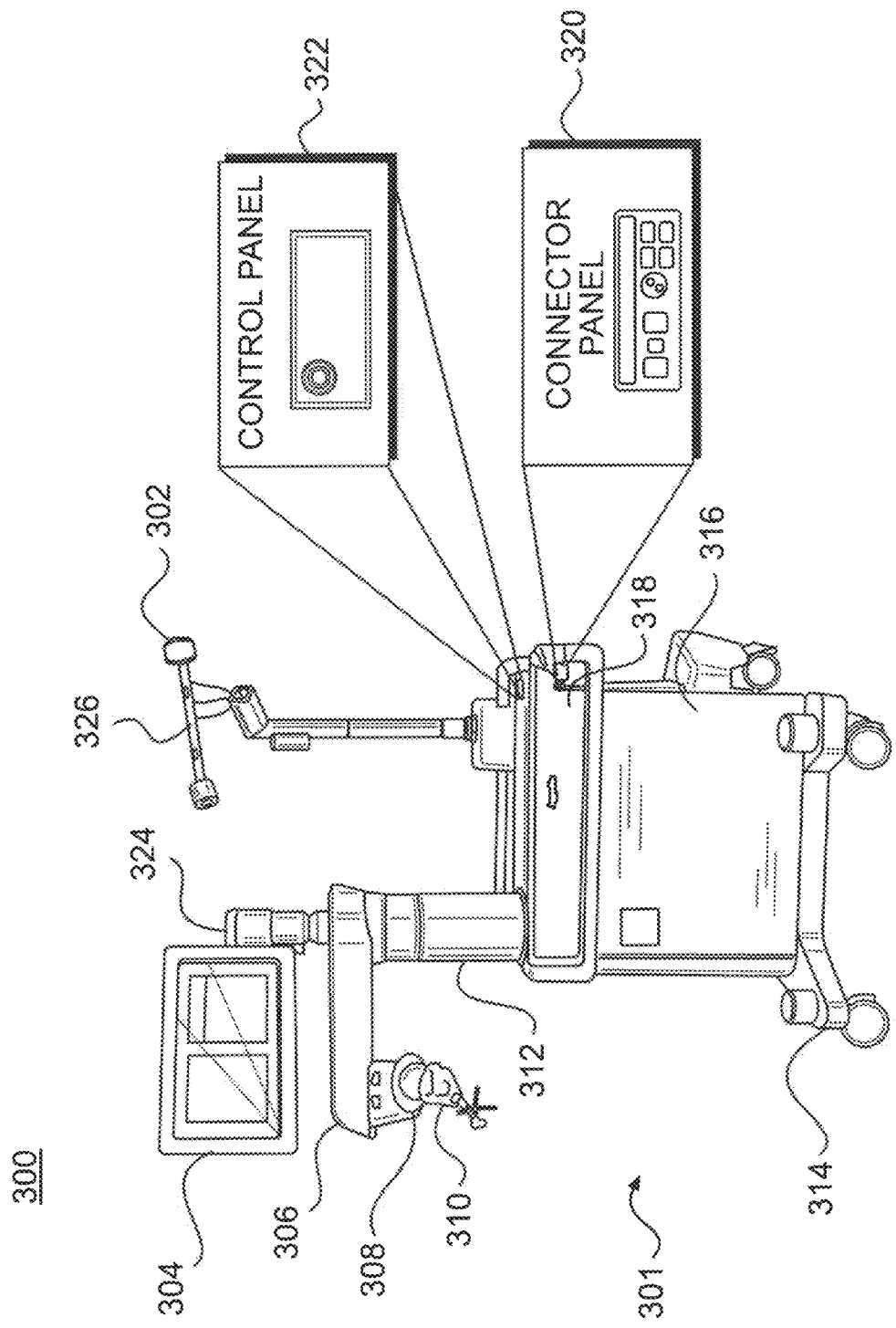
FIG. 3 further illustrates the camera tracking system and the surgical robot configured according to some embodiments.
Figure 4:
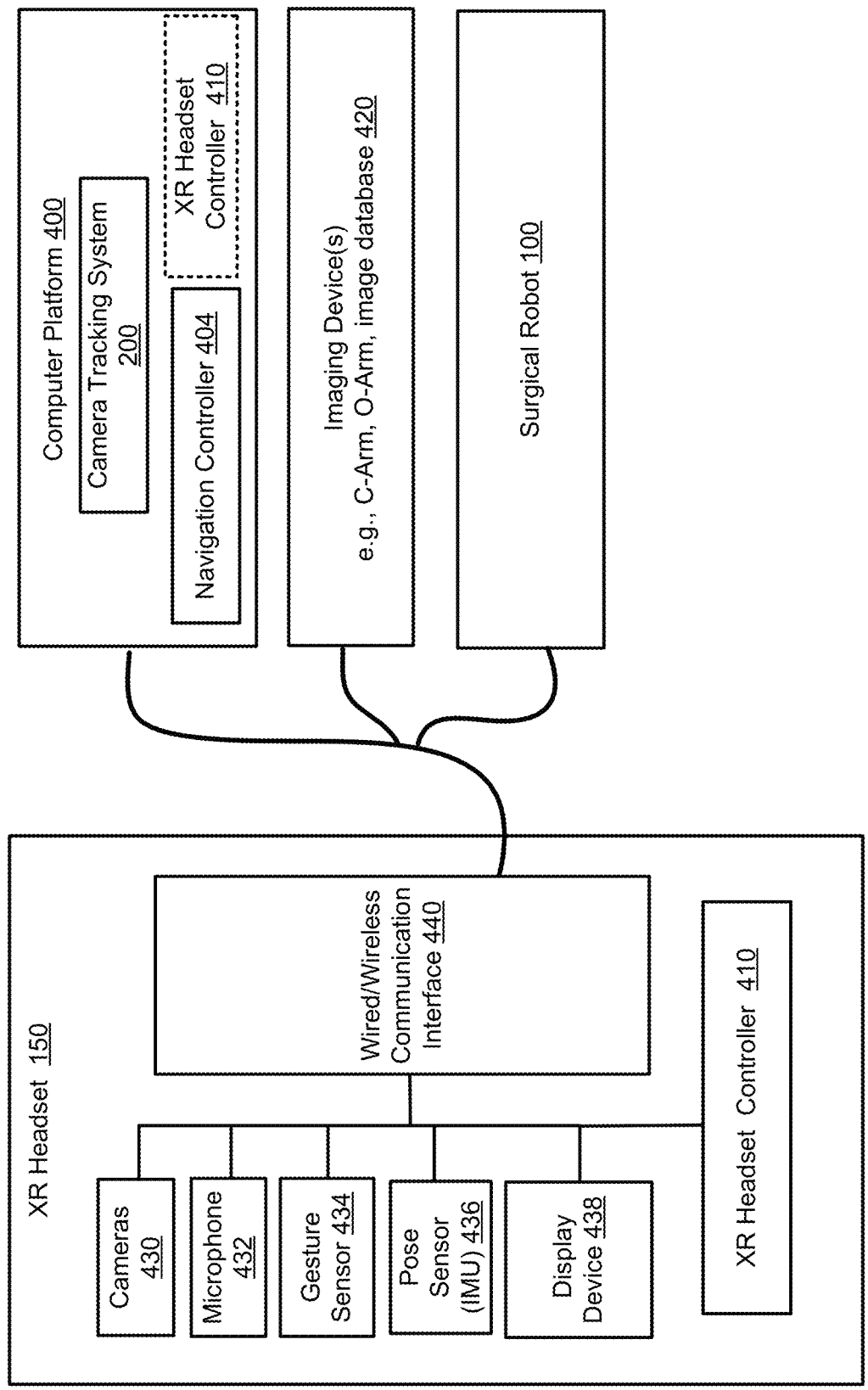
FIG. 4 illustrates a block diagram of a surgical system that includes an XR headset, a computer platform, imaging devices, and a surgical robot which are configured to operate according to some embodiments.
Figure 5:
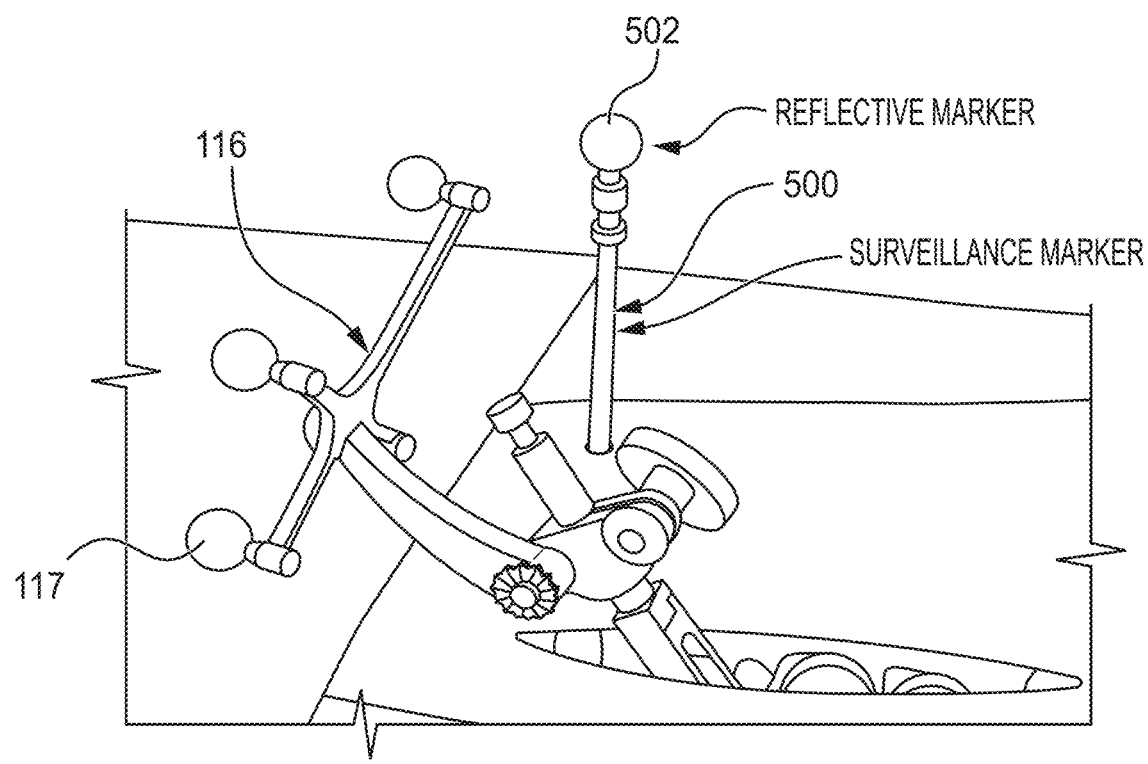
FIG. 5 illustrates a patient reference array (DRB) and a surveillance marker.

FIG. 1 is an overhead view of personnel wearing extended reality (XR) headsets 150 during a surgical procedure in a surgical room that includes a camera tracking system 200 for navigated surgery during a surgical procedure and which may further include a surgical robot 100 for robotic assistance, according to some embodiments. FIG. 2 illustrates the camera tracking system 200 and the surgical robot 100 positioned relative to a patient, according to some embodiments. FIG. 3 further illustrates the camera tracking system 200 and the surgical robot 100 configured according to some embodiments. FIG. 4 illustrates a block diagram of a surgical system that includes an XR headset 150, a computer platform 400, imaging devices 420, and the surgical robot 100 which are configured to operate according to some embodiments. FIG. 5 illustrates a patient reference array 116 (also "dynamic reference base" (DRB)) and a surveillance marker 500.

The XR headset 150 may be configured to augment a real-world scene with computer generated XR images. The XR headset 150 may be configured to provide an augmented reality (AR) viewing environment by displaying the computer generated XR images on a see-through display screen that allows light from the real-world scene to pass therethrough for combined viewing by the user. Alternatively, the XR headset 150 may be configured to provide a virtual reality (VR) viewing environment by preventing or substantially preventing light from the real-world scene from being directly viewed by the user while the user is viewing the computer-generated AR images on a display screen. The XR headset 150 can be configured to provide both AR and VR viewing environments. Thus, the term XR headset can referred to as an AR headset or a VR headset.

Referring to FIGS. 1-5, the surgical robot 100 may include, for example, one or more robot arms 104, a display 110, an end-effector 112, for example, including a guide tube 114, and an end effector reference array which can include one or more tracking markers. A patient reference array 116 (DRB) has a plurality of tracking markers 117 and is secured directly to the patient 210 (e.g., to a bone of the patient 210). A spaced apart surveillance marker 500 (FIG. 5) has a single marker 502 connected to a shaft that is secured directly to the patient 210 at a spaced apart location from the patient reference array 116. Another reference array 170 is attached or formed on an instrument, surgical tool, surgical implant device, etc.

The camera tracking system 200 includes tracking cameras 204 which may be spaced apart stereo cameras configured with partially overlapping field-of-views. The camera tracking system 200 can have any suitable configuration of arm(s) 202 to move, orient, and support the tracking cameras 204 in a desired location, and may contain at least one processor operable to track location of an individual marker and pose of an array of markers. As used herein, the term "pose" refers to the location (e.g., along 3 orthogonal axes) and/or the rotation angle (e.g., about the 3 orthogonal axes) of markers (e.g., DRB) relative to another marker (e.g., surveillance marker) and/or to a defined coordinate system (e.g., camera coordinate system). A pose may therefore be defined based on only the multidimensional location of the markers relative to another marker and/or relative to the defined coordinate system, based on only the multidimensional rotational angles of the markers relative to the other marker and/or to the defined coordinate system, or based on a combination of the multidimensional location and the multidimensional rotational angles. The term "pose" therefore is used to refer to location, rotational angle, or combination thereof.

The tracking cameras 204 may include, e.g., infrared cameras (e.g., bifocal or stereophotogrammetric cameras), operable to identify, for example, active and passive tracking markers for single markers (e.g., surveillance marker 500) and reference arrays which can be formed on or attached to the patient 210 (e.g., patient reference array, DRB), end effector 112 (e.g., end effector reference array), XR headset(s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the markers in order to identify and determine locations of individual markers and poses of the reference arrays in three-dimensions. For example, active reference arrays may include infrared-emitting markers that are activated by an electrical signal (e.g., infrared light emitting diodes (LEDs)), and passive reference arrays may include retro-reflective markers that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track location of a surveillance marker and poses of reference arrays within the XR camera headset field-of-views (FOVs) 152 and 154, respectively. Accordingly, as illustrated in FIG. 1, the location of the surveillance marker and the poses of reference arrays on various objects can be tracked while in the FOVs 152 and 154 of the XR headsets 150 and/or a FOV 600 of the tracking cameras 204.

FIGS. 1 and 2 illustrate a potential configuration for the placement of the camera tracking system 200 and the surgical robot 100 in an operating room environment. Computer-aided navigated surgery can be provided by the camera tracking system controlling the XR headsets 150 and/or other displays 34, 36, and 110 to display surgical procedure navigation information. The surgical robot 100 is optional during computer-aided navigated surgery.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer. This information can be from local sources (e.g., the surgical robot 100 and/or other medical), remote sources (e.g., patient medical image server), and/or other electronic equipment. The camera tracking system 200 may track markers in 6 degrees-of-freedom (6DOF) relative to three axes of a 3D coordinate system and rotational angles about each axis. The XR headsets 150 may also operate to track hand poses and gestures to enable gesture-based interactions with "virtual" buttons and interfaces displayed through the XR headsets 150 and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 150 while positioned on wearers' heads. The patient reference array 116 (DRB) is generally rigidly attached to the patient with stable pitch and roll relative to gravity. This local rigid patient reference 116 can serve as a common reference for reference frames relative to other tracked arrays, such as a reference array on the end effector 112, instrument reference array 170, and reference arrays on the XR headsets 150.

During a surgical procedure using surgical navigation, the surveillance marker 500 is affixed to the patient to provide information on whether the patient reference array 116 has shifted. For example, during a spinal fusion procedure with planned placement of pedicle screw fixation, two small incisions are made over the posterior superior iliac spine bilaterally. The DRB and the surveillance marker are then affixed to the posterior superior iliac spine bilaterally. If the surveillance marker's 500 location changes relative to the patient reference array 116, the camera tracking system 200 may display a meter indicating the amount of movement and/or may display a pop-up warning message to inform the user that the patient reference array may have been bumped. If the patient reference array has indeed been bumped, the registration of the patient reference array to the tracked coordinate system may be invalid and could result in erroneous navigation which is off target.

When present, the surgical robot (also "robot") may be positioned near or next to patient 210. The robot 100 can be positioned at any suitable location near the patient 210 depending on the area of the patient 210 undergoing the surgical procedure. The camera tracking system 200 may be separated from the robot system 100 and positioned at the foot of patient 210. This location allows the tracking camera 200 to have a direct visual line of sight to the surgical area 208. In the configuration shown, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 can comprise a guide tube 114, which is configured to receive and orient a surgical instrument, tool, or implant used to perform a surgical procedure on the patient 210.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axis, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a six DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 150 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Reference arrays of markers can be formed on or connected to robot arms 102 and/or 104, the end-effector 112 (e.g., end-effector array 114 in FIG. 2), and/or a surgical instrument (e.g., instrument array 170) to track poses in 6 DOF along 3 orthogonal axes and rotation about the axes. The reference arrays enable each of the marked objects (e.g., the end-effector 112, the patient 210, and the surgical instruments) to be tracked by the tracking camera 200, and the tracked poses can be used to provide navigated guidance during a surgical procedure and/or used to control movement of the surgical robot 100 for guiding the end-effector 112 and/or an instrument manipulated by the end-effector 112.

Referring to FIG. 3 the surgical robot 100 may include a display 110, upper arm 102, lower arm 104, end-effector 112, vertical column 312, casters 314, a table 318, and ring 324 which uses lights to indicate statuses and other information. Cabinet 106 may house electrical components of surgical robot 100 including, but not limited, to a battery, a power distribution module, a platform interface board module, and a computer. The camera tracking system 200 may include a display 36, tracking cameras 204, arm(s) 202, a computer housed in cabinet 330, and other components.

In computer-assisted navigated surgeries, perpendicular 2D scan slices, such as axial, sagittal, and/or coronal views, of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System:

FIG. 4 illustrates a block diagram of a surgical system that includes an XR headset 150, a computer platform 400, imaging devices 420, and a surgical robot 100 which are configured to operate according to some embodiments.

The imaging devices 420 may include a C-arm imaging device, an O-arm imaging device, and/or a patient image database. The XR headset 150 provides an improved human interface for performing navigated surgical procedures. The XR headset 150 can be configured to provide functionalities, e.g., via the computer platform 400, that include without limitation any one or more of: identification of hand gesture based commands, display XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit (IMU)) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field of view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes the camera tracking system 200 which may be connected to a computer platform 400 for operational processing and which may provide other operational functionality including a navigation controller 404 and/or of an XR headset controller 410. The surgical system may include the surgical robot 100. The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector of the surgical robot 100, where the steering information is displayed through the display device 438 of the XR headset 150 and/or another display device to indicate where the surgical tool and/or the end effector of the surgical robot 100 should be moved to perform the surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the I/O-arm imaging device, the patient image database, and/or to other medical equipment through the wired/wireless interface 440.

The surgical system may include a XR headset controller 410 that may at least partially reside in the XR headset 150, the computer platform 400, and/or in another system component connected via wired cables and/or wireless communication links. Various functionality is provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from tracking cameras from the cameras 430 (tracking cameras), signals from the microphone 1620, and/or information from the pose sensor 436 and the gesture sensor 434, to generate information for display as XR images on the display device 438 and/or as other for display on other display devices for user viewing. Thus, the XR headset controller 410 illustrated as a circuit block within the XR headset 150 is to be understood as being operationally connected to other illustrated components of the XR headset 150 but not necessarily residing within a common housing or being otherwise transportable by the user. For example, the XR headset controller 410 may reside within the computer platform 400 which, in turn, may reside within the cabinet 330 of the camera tracking system 200, the cabinet 106 of the surgical robot 100, etc.

Identifying Phantom Markers Imaged by Tracking Cameras:

Regardless of the workflow for registering a stray maker, such as the surveillance marker, the presence of "phantom" markers can be problematic. Phantom markers occur as a result of epipolar stereo tracking ambiguity, reflections and other environmental conditions, and do not represent the 3D location of a stray actual marker. A stray actual marker is a physical marker, e.g., surveillance marker, that appears in frames of tracking data from tracking cameras and is intended to be tracked by the camera tracking system, but which has not yet been registered with the camera tracking system. If a phantom marker also appears in the frames, the presence of the phantom markers can make it infeasible to register the stray actual marker with just a single button press, because the system does not know which of the marker candidates to use. The camera tracking system also becomes susceptible to error if, for example, the actual marker is not present (e.g., obscured from view) while only one phantom is present in the frames, which can cause the single button press to trigger incorrect registration of the phantom marker as the actual marker. Alternatively, if the user happens to accidentally point a tracked tool at a point in space where a phantom marker is closer to the tip than the stray actual marker or inadvertently gesture to identify a phantom adjacent to the intended candidate, the camera tracking system could incorrectly register the phantom marker as the actual marker.

As explained above, various embodiments of the present disclosure are directed to providing operations by the camera tracking system 200 which may improve registration of stray markers, such as the surveillance marker 500 in FIG. 5, when phantom markers are present in frames of tracking data from the tracking cameras 204. Phantom markers can occur as a result of epipolar stereo tracking ambiguity, reflections and other environmental conditions, and do not represent 3D locations of actual stray markers. Other phantom markers occur due to stereo ambiguity between tracking cameras 204 when multiple actual markers appear on the same vertical row of the image sensors of the tracking cameras 204. It has been determined that a characteristic of phantom markers is that they do not move through 3D space like actual markers when the tracking cameras 204 are moved to point toward the scene from different perspectives, because the phantom markers are not anchored to the camera coordinate system in the same way as actual markers. For example, rolling the tracking cameras 204 slightly to cause a small change in perspective of the tracking cameras 204 can break stereo ambiguity and cause many phantoms to disappear when determining 3D locations of stray actual markers in frames of tracking data. Phantom marker visibility is generally less consistent than that of stray actual markers, meaning that phantom markers may be visible only from one particular perspective of the tracking cameras but from no other perspective.

Some embodiments are directed to operations which classify stray markers as "assigned" status, "unknown" status, and/or "phantom" status in a frame of tracking data from tracking cameras on a tracking bar, XR headset, etc. Stray markers may be filtered so that registration is only performed on a stray marker which does not have phantom status, such as when a user registers a surveillance marker. By eliminating any phantom status strays being used in the registration process, the operations may increase the incidence of scenarios where the surveillance marker can be selected through a user interface, e.g., by a user-selectable registration button, instead of requiring tracking of a user-posed pointing tool and which can avoid or prevent various errors such as described above. These operations may utilize the inconsistent visibility and location of phantoms markers versus actual stray markers.

In some embodiments, both the patient reference array (e.g., DRB) and surveillance marker are viewed from more than one perspective of the tracking cameras, e.g., arranged in a stereo configuration with partially overlapping field-of-view. More than one perspective can be obtained by moving the tracking cameras to provide rotational and/or linear location offset between frames of tracking data received from the tracking cameras. In one scenario, a user affixes a DRB and a surveillance marker to the patient and then moves the tracking cameras on a camera bar to provide more optimal positioning for tracking of markers during a surgical procedure. While the tracking cameras are being moved and the surveillance marker and DRB are visible, operations are performed to identify candidate markers in frames of tracking data from the tracking cameras, and to process the candidate markers into various different statuses, which are referred to without limitation as, e.g., assigned status, unknown status, and ambiguous status.

In one operational embodiment, when a frame is received from the tracking cameras, the position of the DRB in the camera coordinate system is recorded along with all stray makers (also "strays") visible from this perspective of the tracking cameras. For easier comparison to other frames, locations of stray markers are recorded relative to the DRB, not in the camera coordinate system in accordance with one embodiment. Next, the set of previous camera positions and the corresponding sets of stray markers are compared to the current frame. If the current camera orientation for a received frame is the same (e.g., within a tolerance threshold, such as less than 10 mm or 1 degree) as a previous camera orientation for a previously received frame, the stray markers from the stored set are compared to the previous set for this orientation and any stray markers now present that were not present previously are included in a set for further processing and stored. This operation accounts for actual stray markers that may have been blocked from line of sight in a previous frame. If this camera orientation is different than any previous orientation (e.g., more than the tolerance threshold), any stray markers common to both sets (e.g., difference in position relative to DRB<1 mm) can be classified with unknown status for further processing to determine whether they should be designated as phantom status, while any candidate markers not common to both sets may be more likely to be phantom and may not be included in further processing or may be processed to have an increased likelihood of being designated as phantom status. As the tracking cameras continue to move and more orientations are recorded, their respective sets of stray markers are compared to the sets of stray markers for all other orientations. In some embodiment, only stray markers that are present in greater than some minimum number of orientations are included in a candidate registration set which is used to perform registration of one or more markers in the set. With these operations, it is possible for stray markers to have status changed from unknown to phantom or vice versa depending on in how many different tracking camera orientations they were identified in the corresponding received frames.

The operation for changing stray markers' status, based on how many frames from different tracking camera orientations they are identified in, can be directed to situations where phantom markers are identified in frames from more than one tracking camera perspective by chance and where there may be frames where the actual stray markers are obscured or not visible to the tracking cameras for some reason. It would be undesirable for such frames to cause the actual stray markers to inadvertently be designated as phantom strays thereafter.

Figure 7:
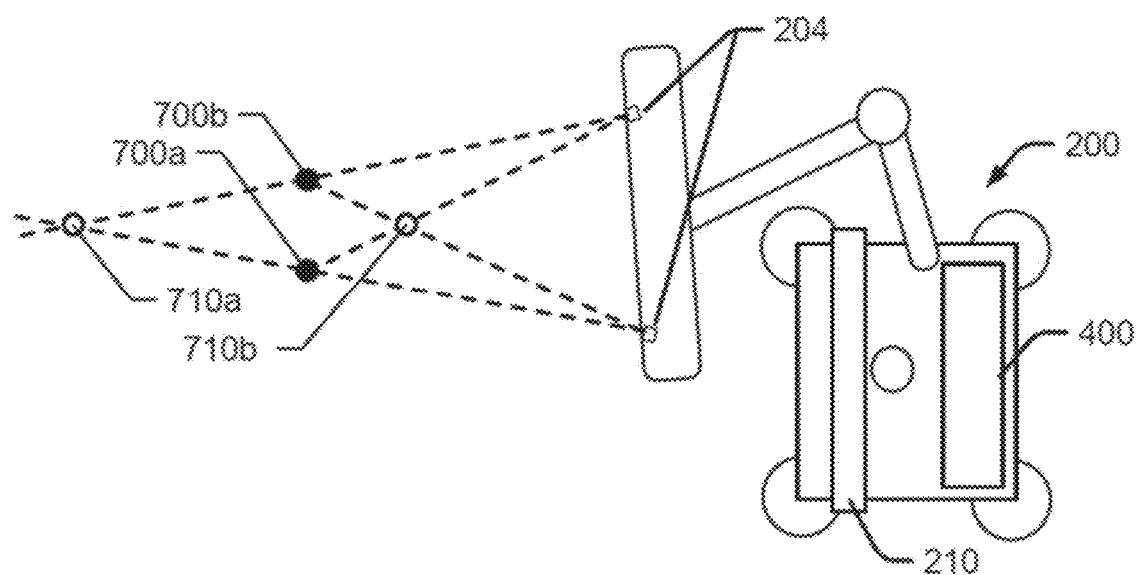
FIG. 7 illustrates the camera tracking system with spaced apart tracking cameras which are viewing actual tracking markers on the same epipolar line as an imaging plane of the tracking cameras.

Some further embodiments are directed to identifying phantom markers that can arise specifically from epipolar ambiguity of the tracking cameras when determining locations of actual stray markers, such as a surveillance marker. FIG. 7 illustrates the camera tracking system 200 with spaced apart tracking cameras 204, which are viewing actual tracking markers 700a and 700b, and which are assumed to be on the same epipolar, e.g., horizontal, line as an imaging plane of the tracking cameras 204. Phantom markers 710a and 710b arise due to epipolar ambiguity of the tracking cameras 204 when determining locations of stray markers, including the actual tracking markers 700a and 700b, in frames received from the tracking cameras 204, based on the relative spacing and orientation of the imaging planes of the tracking cameras 204.

Figure 6:
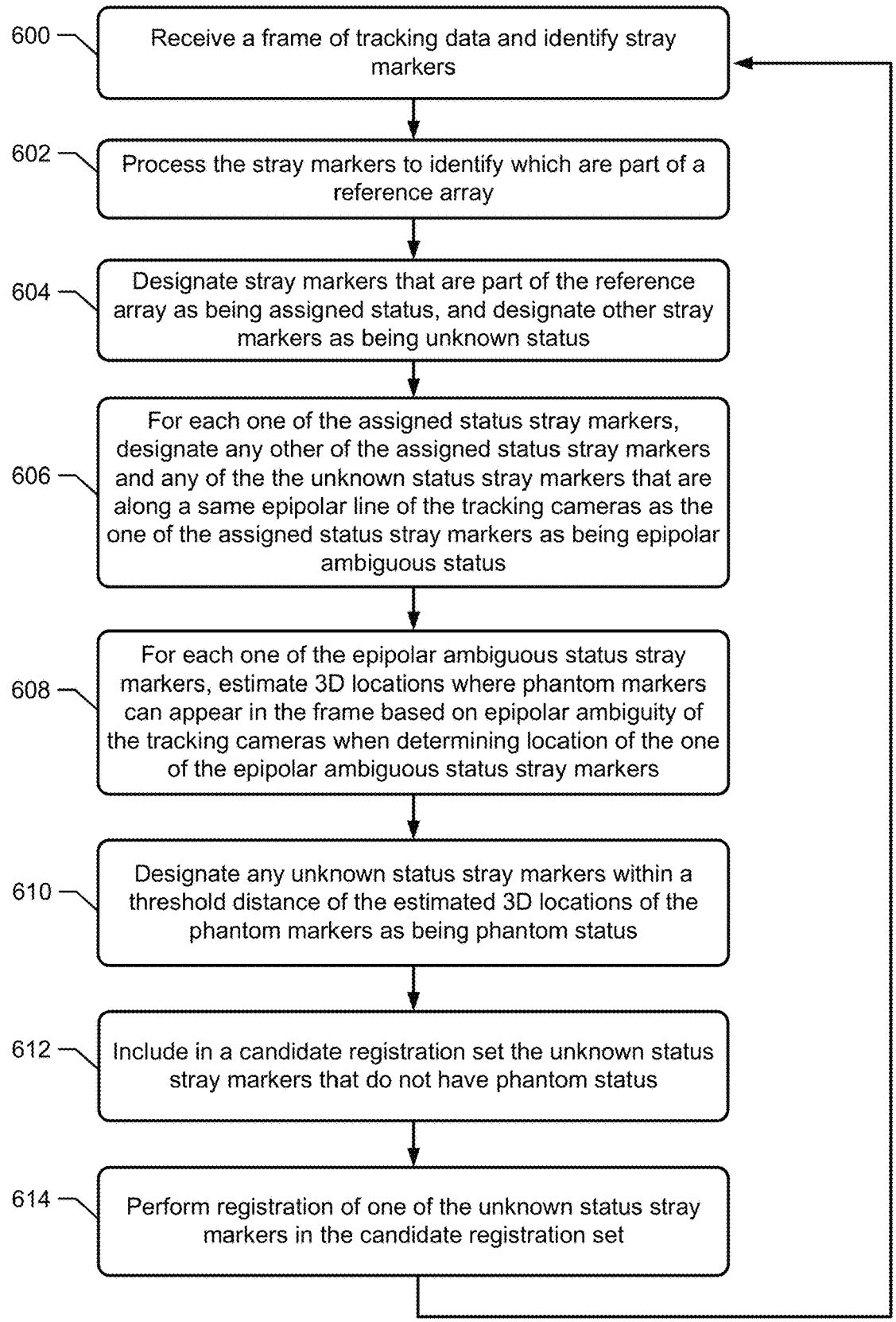
FIG. 6 illustrates a flowchart of operations that may be performed by a camera tracking system for computer assisted navigation during surgery according to some embodiments.

FIG. 6 illustrates a flowchart of operations that may be performed by a camera tracking system for computer assisted navigation during surgery in accordance with some other embodiments.

Referring to FIG. 6, the operations receive 600 a stream of frames of tracking data from tracking cameras configured with a partially overlapping field-of-view. As the frames are received, the operations process a present frame to identify 600 stray markers in the frame. The identification may determine 3D locations of the stray markers. The operations process the stray markers to identify 602 which of the stray markers are part of a reference array, such as a DRB. The operations designate 604 stray markers that are part of the reference array as being assigned status. The operations designate 606 stray markers that are not part of the reference array as being unknown status. The terms "assigned status" and "unknown status" are used in a non-limiting manner only to differential one status from the other status. Accordingly, the term assigned status may be interchangeably replaced with the term first status and, similarly, the term unknown status may be replaced with the term second status.

For each one of the assigned status stray markers, the operations designate 606 any other of the assigned status stray markers and any of the unknown status stray markers that are along a same epipolar line of the tracking cameras as the one of the assigned status stray markers as being epipolar ambiguous status. For each one of the epipolar ambiguous status stray markers, the operations estimate 608 3D locations where phantom markers can appear in the frame based on epipolar ambiguity of the tracking cameras when determining location of the one of the epipolar ambiguous status stray markers. The operations designate 610 any of the unknown status stray markers within a threshold distance of the estimated 3D locations of the phantom markers as being phantom status, and include 612 in a candidate registration set the unknown status stray markers that do not have phantom status.

The threshold distance value may be a function of the epipolar ambiguity of the tracking cameras. In some embodiments, the threshold distance is not greater than 2 millimeters so that, for example, if a unknown status stray markers is within a 2 millimeter cubic box centered at the computed 3D location of the phantom marker, that unknown status stray marker is designated 610 as phantom status.

The operations may further perform registration of one or more of the unknown status stray markers in the candidate registration set. For example, as will be explained in further detail below, when only one unknown status stray marker exists in the candidate registration set, the camera tracking system may display a registration indicia that can be selected by a user to register the unknown status stray marker as a surveillance marker or another defined marker.

Because phantom markers should not be allowed to be registered, the operations may prevent registration of any of the phantom status stray markers.

The camera tracking system may operate to track location of the registered one of the unknown status stray markers relative to the reference array. For example, the operations may track location of the surveillance marker relative to the DRB to determine if the DRB and/or the surveillance marker has moved, such as from being bumped by a user, and may trigger a warning notification to be generated to the user of a threshold movement is identified.

The operations may limit registration 614 to being performed on only unknown status stray markers that are identified in at least a threshold number of the plurality of frames. The operations may further limit registration 614 to being performed on only unknown status stray markers that are identified in at least the threshold number of the plurality of frames which have been determined to have camera movement offsets greater than a threshold movement offset.

The operations may determine a movement offset of the tracking cameras between receipt of the present frame and receipt of a previous frame or, in a further embodiment, receipt of any of the previously received frames. Thus, the "previous frame" may be the frame received in sequence immediately before the present frame or may be any of the frames that were received in the stream before the present frame. The determination of the movement offset may include determining a rotational offset of the tracking cameras and/or a linear location offset of the tracking cameras.

The threshold movement offset may be, for example, defined as more than 10 millimeters of linear location offset of the tracking cameras and/or defined as more than one degree of rotational offset of the tracking cameras between capturing the present frame and capturing a previous frame. The movement offset may be determined based on comparing the 3D locations of the candidate markers of the present frame set to the 3D locations of the candidate markers of the previous frame set or, in some embodiments, to the 3D locations of the candidate markers in any of the frame sets that were identified from earlier frames in the stream. The decision of whether the movement offset is less than the threshold movement offset, may include comparing the 3D locations of the candidate markers of the present frame set to the 3D locations of the candidate markers of any of the previously received frame sets in order to, for example, determine whether the present orientation of the tracking cameras is not sufficiently different from an earlier orientation of the tracking cameras.

In one embodiment, the operations determine 3D locations of the stray markers, determine a camera movement offset of the tracking cameras between receipt of the frame and receipt of a previous frame, and based on when the camera movement offset is less than a threshold movement offset, not perform the estimation 608 of 3D locations where phantom markers can appear in the frame based on epipolar ambiguity of the tracking cameras. For example, the operations may wait for the camera movement offset to be at least the threshold movement offset before processing a next frame to perform operations 608-612.

Example Registration Operations:

Some further embodiments are directed to utilizing the operations of FIG. 6 to enable the camera tracking system to automatically register or to provide a simplified user interface for triggering registration of a candidate marker as a defined type of marker, such as a surveillance marker.

For example, after unknown status stray markers that do not have phantom status have been identified (included 612 in the candidate registration set), the operations may generate a user interface through which a user provides at least one command to cause registration 614 of those stray markers for location tracking by the camera tracking system. The operation may then enable tracking of the location of the one of the candidate markers as a surveillance marker tracked relative to a reference array.

For example, when the candidate registration set contains a single candidate marker, e.g., a single unknown status stray marker that do not have phantom status, the operations may display a user-selectable indicia that can be selected by a user to trigger registration of the candidate marker as a surveillance marker. Because the surveillance marker should be positioned relatively closely to a DRB in order to allow tracking of any movement of the DRB and/or surveillance marker, e.g., due to being bumped, the operations may require that single single unknown status stray marker without phantom status to be within a threshold distance of the DRB or another defined reference array before displaying the user-selectable indicia allowing the user to trigger registration of that stray marker as a surveillance marker. The threshold distance from the DRB or other defined reference array may be, for example, less than 30 centimeters, in accordance with some embodiments.

For example, in one embodiment, the camera tracking system determines a particular one of the stray markers included in the candidate registration set satisfies a defined rule for corresponding to a surveillance marker such as by being the only stray marker in the candidate registration set. The camera tracking system can respond to the determination by displaying a registration initiation indicia selected by a user to trigger registration of the particular one of the stray markers as the surveillance marker. Once registration of the stray marker as the surveillance marker is complete, the camera tracking system can then track location of the surveillance marker relative to the DRB or other reference array. In a further embodiment, to satisfy the defined rule the particular one of the candidate markers included in the candidate registration set needs to be determined to be within a threshold distance from the reference array. As explained above, Because the surveillance marker should be positioned relatively closely to a DRB in order to allow tracking of any movement of the DRB and/or surveillance marker, e.g., due to being bumped, the operations may require the single stray marker to be within a threshold distance of the DRB or another defined reference array before displaying the user-selectable indicia allowing the user to trigger registration of the stray marker as a surveillance marker. The threshold distance from the DRB or other defined reference array may be, for example, less than 30 centimeters, in accordance with some embodiments.

The camera tracking system may display visual cues to a user to facilitate involvement in some of the operations described in FIG. 6.

In one embodiments, as part of operations of FIG. 6, the camera tracking system may display a first type of graphical object at locations of assigned status stray markers and display a second type of graphical object at locations of unknown status stray markers, where the first type of graphical object has a different shape and/or color than the second type of graphical object.

The camera tracking system may provide guidance to a user to begin and/or end movement of the tracking cameras to facilitate registration and tracking of markers. For example, in one embodiment, the system displays an indication to a user that further movement of the tracking cameras is not needed for registration, responsive to determining that the stray marker(s) included in the candidate registration set satisfies a defined rule. The defined rule may correspond to determining that the stray marker(s) have been present in at least a threshold number of previous frames, may further include determining that those threshold number of previous frames have at least a threshold offset relative to each other.

In some other embodiments, the camera tracking system may determine locations of the the unknown status stray markers, and display graphical indications overlaid on at least one of the frames at the locations of the unknown status stray markers. The graphical indications may be overlaid at locations in at least one of the frames determined based on the determined 3D locations. The operations receive a user selection of one of the graphical indications, and perform registration of one of the unknown status stray markers with the location corresponding to the selected one of the graphical indications.

The operations may receive the user selection of one of the graphical indications through a touch screen interface, such as by the user touch-selecting one of the graphical indications to register the one of the unknown status stray markers with the location corresponding to the selected one of the graphical indications.

Alternatively or additionally, the operations may display a graphical representation of a tool being tracked by the camera tracking system while the tool is manipulated by the user. The operations receive the user selection of the one of the graphical indications based on determining a tracked location on the tool is within a threshold selection distance from the location of the one of the graphical indications while a further defined condition is satisfied. Thus, for example, the user can indicate which of the stray markers is to be registered as the surveillance marker by positioning an end of the displayed graphically representation of the tool within the threshold selection distance of the displayed graphical indication associated with the to-be-selected stray marker.

As explained above, once the stray marker(s) are registered with the camera tracking system, the camera tracking system may then perform operations for navigated surgical procedures. The operations can include to track pose of an instrument relative to the registered marker, and generate steering information based on comparison of the pose of the instrument relative to a planned pose of the instrument. The steering information can indicate where the instrument needs to be moved and angularly oriented to become aligned with the planned pose when performing a surgical procedure.

Another embodiment for a method to eliminate stray markers from consideration is to assess whether the marker is located in an untenable place. For example, does the stray maker appear to be on the surface of the robot arm, inside the patient, or on the bed? If so, it is most likely a phantom stray and can be eliminated from the set of candidates, e.g., not included in the candidate registration set. Position of a stray marker relative to the robot or patient requires knowledge of the location of these other structures. Because the robot arm is tracked and can have position sensors in each joint, the operations may compute the location of the arm surface based on these tracked parameters and compare locations of the surfaces of the robot arm to locations of each stray marker. To determine whether a tracked location is inside the patient, the operations may use the registration of the CT scan volume to the tracking cameras and to use planned implant locations, image processing, machine vision, or a manual identification of surface points to compute where the patient is positioned relative to the cameras.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A camera tracking system for computer assisted navigation during surgery, comprising at least one processor operative to:
   receive a stream of frames of tracking data from tracking cameras configured with a partially overlapping field-of-view; and
   for each of a plurality of the frames in the stream,
      identify stray markers in the frame,
      identify which of the stray markers are part of a reference array,
      designate stray markers that are part of the reference array as being assigned status,
      designate stray markers that are not part of the reference array as being unknown status,
      for each one of the assigned status stray markers, designate any other of the assigned status stray markers and any of the unknown status stray markers that are along a same epipolar line of the tracking cameras as the one of the assigned status stray markers as being epipolar ambiguous status,
      for each one of the epipolar ambiguous status stray markers, estimate 3D locations where phantom markers can appear in the frame based on epipolar ambiguity of the tracking cameras when determining location of the one of the epipolar ambiguous status stray markers,
      designate any of the unknown status stray markers within a threshold distance of the estimated 3D locations of the phantom markers as being phantom status, and
      include in a candidate registration set the unknown status stray markers that do not have phantom status.

2. The camera tracking system of claim 1, wherein the at least one processor is further operative to:
   perform registration of one of the unknown status stray markers in the candidate registration set.

3. The camera tracking system of claim 2, wherein the at least one processor is further operative to:
   prevent registration of any of the phantom status stray markers.

4. The camera tracking system of claim 2, wherein the at least one processor is further operative to:
   track location of the registered one of the unknown status stray markers relative to the reference array.

5. The camera tracking system of claim 2, wherein the at least one processor is further operative to:
   limit registration to being performed on only unknown status stray markers that are identified in at least a threshold number of the plurality of frames which have been determined to have camera movement offsets greater than a threshold movement offset.

6. The camera tracking system of claim 1, wherein the threshold distance is not greater than 2 millimeters.

7. The camera tracking system of claim 1, wherein the at least one processor is further operative to:
   display a first type of graphical object at locations of assigned status stray markers; and
   display a second type of graphical object at locations of unknown status stray markers, wherein the first type of graphical object has a different shape and/or color than the second type of graphical object.

8. The camera tracking system of claim 1, wherein the at least one processor is further operative to:
   determine whether a particular one of the unknown status stray markers included in the candidate registration set satisfies a defined rule for corresponding to a surveillance marker;
   display a registration initiation indicia selectable by a user to trigger registration of the particular one of the unknown status stray markers as the surveillance marker; and
   track location of the surveillance marker relative to the reference array.

9. The camera tracking system of claim 8, wherein the reference array and the surveillance marker are configured to be affixed to a patient, and the at least one processor is further operative to:

track pose of an instrument relative to the reference array; and generate steering information based on comparison of the pose of the instrument relative to a planned pose of the instrument, wherein the steering information indicates where the instrument needs to be moved and angularly oriented to become aligned with the planned pose when performing a surgical procedure.

10. The camera tracking system of claim 8, wherein to satisfy the defined rule the particular one of the unknown status stray markers included in the candidate registration set is within a threshold registration distance from the reference array.

11. The camera tracking system of claim 1, wherein the at least one processor is further operative to:
determine locations of the unknown status stray markers;
display graphical indications overlaid on at least one of the frames at the locations of the unknown status stray markers;
receive a user selection of one of the graphical indications; and
perform registration of one of the unknown status stray markers with the location corresponding to the selected one of the graphical indications.

12. The camera tracking system of claim 11, wherein the at least one processor is further operative to receive the user selection of one of the graphical indications through a touch screen interface.

13. The camera tracking system of claim 12, wherein the at least one processor is further operative to:
display a graphical representation of a tool being tracked by the camera tracking system while manipulated by the user; and
receive the user selection of the one of the graphical indications based on determining whether a tracked location on the tool is within a threshold selection distance from the location of the one of the graphical indications while a further defined condition is satisfied.

14. The camera tracking system of claim 1, wherein the at least one processor is further operative to:
determine three-dimensional (3D) locations of the stray markers,
determine a camera movement offset of the tracking cameras between receipt of the frame and receipt of a previous frame, and
based on when the camera movement offset is less than a threshold movement offset, not perform the estimation of 3D locations where phantom markers can appear in the frame based on epipolar ambiguity of the tracking cameras.

15. The camera tracking system of claim 14, wherein the determination of the camera movement offset determines rotational offset of the tracking cameras.

16. The camera tracking system of claim 14, wherein the determination of the camera movement offset determines linear location offset of the tracking cameras.

17. A method by a camera tracking system for computer assisted navigation during surgery, the method comprising:
receiving a stream of frames of tracking data from tracking cameras configured with a partially overlapping field-of-view; and
for each of a plurality of the frames in the stream,
identifying stray markers in the frame,
identifying which of the stray markers are part of a reference array,
designating stray markers that are part of the reference array as being assigned status,
designating stray markers that are not part of the reference array as being unknown status,
for each one of the assigned status stray markers, designate any other of the assigned status stray markers and any of the unknown status stray markers that are along a same epipolar line of the tracking cameras as the one of the assigned status stray markers as being epipolar ambiguous status,
for each one of the epipolar ambiguous status stray markers, estimating 3D locations where phantom markers can appear in the frame based on epipolar ambiguity of the tracking cameras when determining location of the one of the epipolar ambiguous status stray markers,
designating any of the unknown status stray markers within a threshold distance of the estimated 3D locations of the phantom markers as being phantom status, and
including in a candidate registration set the unknown status stray markers that do not have phantom status.

18. The method of claim 17, further comprising:
performing registration of one of the unknown status stray markers in the candidate registration set.

19. The method of claim 18, further comprising:
limiting registration to being performed on only unknown status stray markers that are identified in at least a threshold number of the plurality of frames which have been determined to have camera movement offsets greater than a threshold movement offset.

20. The method of claim 17, further comprising:
determining whether a particular one of the unknown status stray markers included in the candidate registration set satisfies a defined rule for corresponding to a surveillance marker;
displaying a registration initiation indicia selectable by a user to trigger registration of the particular one of the unknown status stray markers as the surveillance marker; and
tracking location of the surveillance marker relative to the reference array.

* * * * *